(12) United States Patent
Guala

(10) Patent No.: US 6,390,130 B1
(45) Date of Patent: May 21, 2002

(54) VALVE FOR MEDICAL INFUSION LINES AND THE LIKE

(75) Inventor: Gianni Guala, Turin (IT)

(73) Assignee: Industrie Borla SpA (IT)

( * ) Notice: Subject to any disclaimer, the term of this patent is extended or adjusted under 35 U.S.C. 154(b) by 0 days.

(21) Appl. No.: 09/706,109

(22) Filed: Nov. 3, 2000

(30) Foreign Application Priority Data

Nov. 12, 1999 (IT) .......................................... TO99A0974

(51) Int. Cl.[7] .......................... F16K 15/14; A61M 39/24
(52) U.S. Cl. ....................................... 137/859; 604/247
(58) Field of Search ............................... 137/843, 859, 137/269.5, 515.5; 604/247

(56) References Cited

U.S. PATENT DOCUMENTS

| 2,758,609 A | * | 8/1956 | Dickert et al. | 137/515.5 |
| 3,084,707 A | * | 4/1963 | Frye | 137/859 |
| 3,270,771 A | * | 9/1966 | Morgan et al. | 137/859 |
| 4,712,583 A | * | 12/1987 | Pelmulder et al. | 137/859 |
| 5,025,829 A | * | 6/1991 | Edwards et al. | 137/512 |
| 5,617,897 A | * | 4/1997 | Myers | 137/859 |
| 5,727,594 A | * | 3/1998 | Choksi | 137/859 |
| 5,771,935 A | * | 6/1998 | Myers | 137/859 |
| 6,089,272 A | * | 2/1999 | Brand et al. | 137/859 |

FOREIGN PATENT DOCUMENTS

EP          0 247 824          2/1987

* cited by examiner

Primary Examiner—John Rivell
Assistant Examiner—Ramesh Krishnamurthy
(74) Attorney, Agent, or Firm—TraskBritt, P.C.

(57) ABSTRACT

A check valve for medical infusion lines and the like, including a diaphragm made of elastic material inserted between a first and a second tubular connector and acting on an annular valve seat to keep the check valve normally closed. The diaphragm includes an annular peripheral section and a central disc, connected to the peripheral section via a crown of spaced-out arms. The disc is moulded with a thin, axially projecting, circumferential sealing lip on one face or, more conveniently, on both faces thereof.

25 Claims, 8 Drawing Sheets

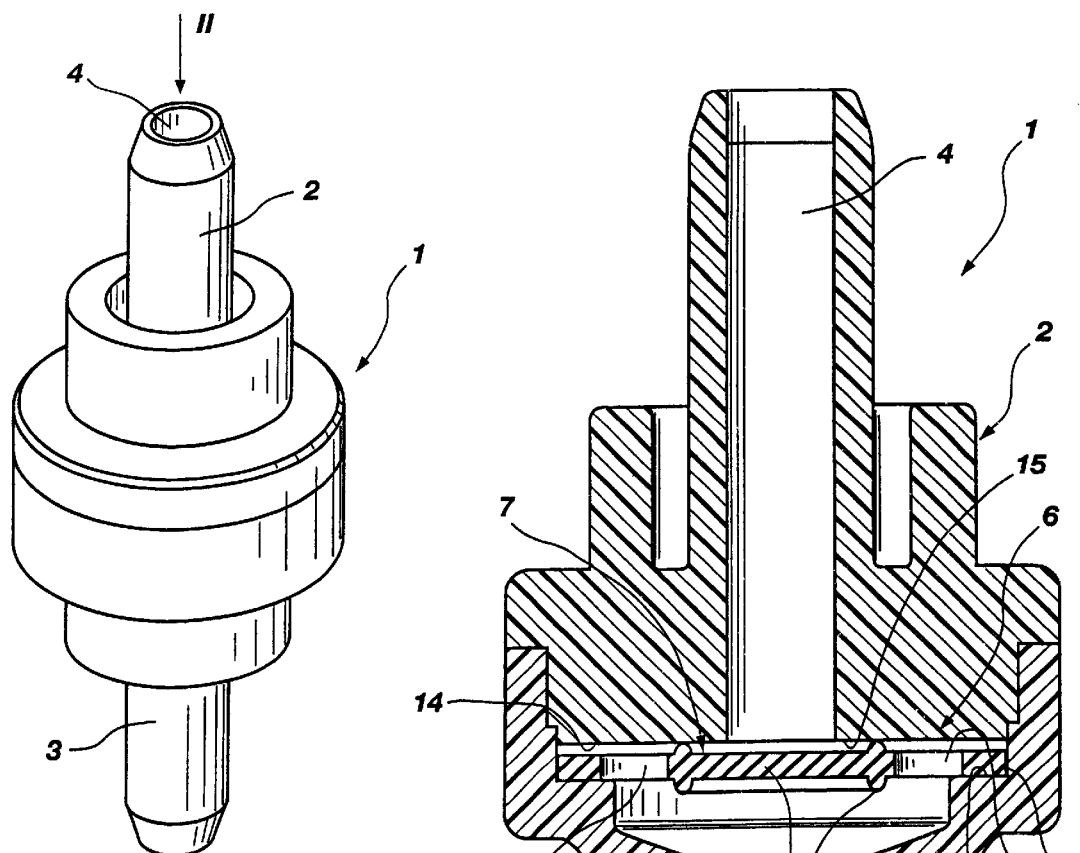
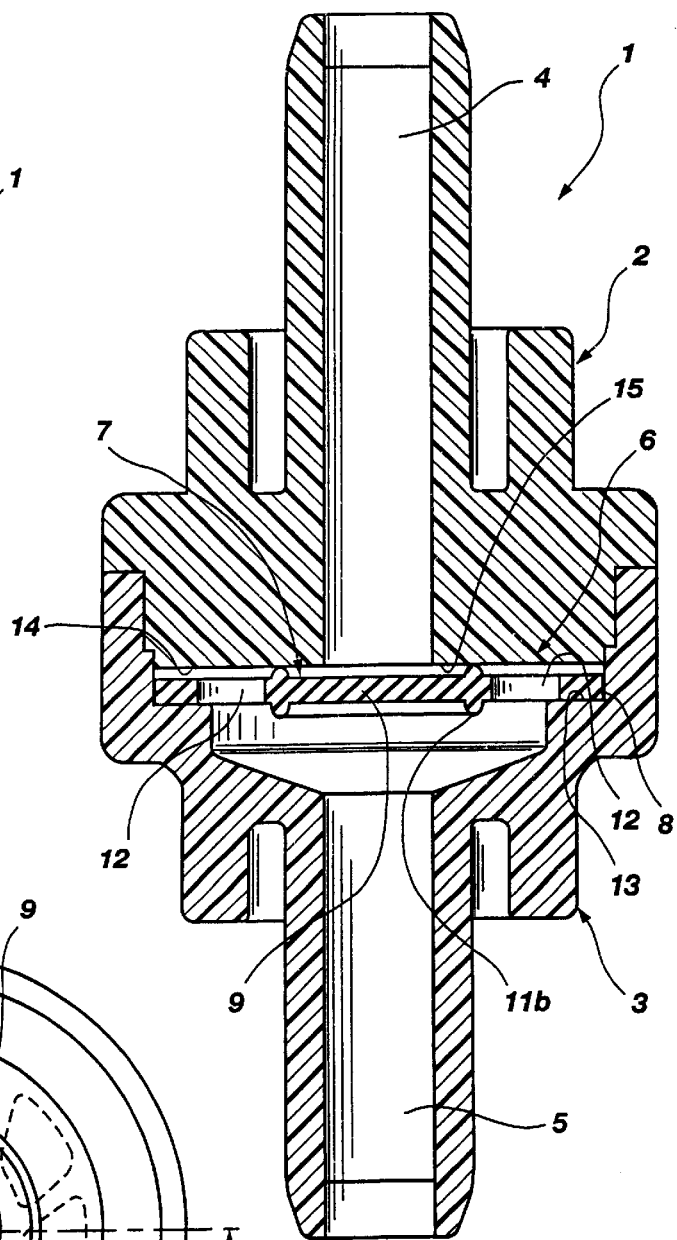
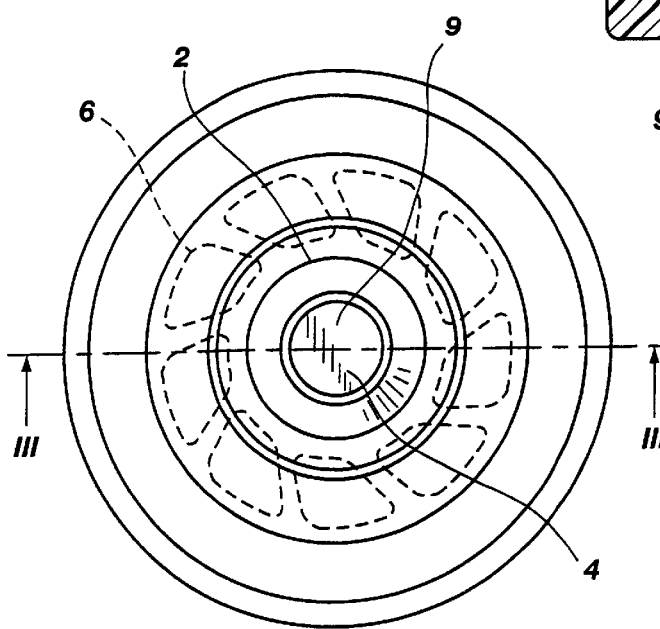
Fig. 1A
Fig. 2A
Fig. 3A

VALVE FOR MEDICAL INFUSION LINES AND THE LIKE

BACKGROUND OF THE INVENTION

The present invention refers to check valves for medical infusion lines and the like.

Such check (or non return) valves normally incorporate a first and a second tubular element that respectively define an upstream and a downstream passageway, mutually coaxial to each other and with an elastically deformable diaphragm placed transversally between them. This diaphragm cooperates with the annular seat of the said first tubular element to form a fluid seal that maintains the check valve in the normally closed position, and in which a predetermined fluid pressure in the said upstream passageway causes a deflection of the diaphragm and consequent opening of the check valve.

Such check valves must meet a series of critical requirements: in the first place, they must normally be closed and must only open, continuously or intermittently, when the pressure in the upstream passageway is higher than a predetermined threshold, normally of small entity e.g. 0.01–0.02 bar. The check valve must also be capable of preventing any reflux from the downstream passageway to the upstream passageway with utmost security, i.e. it must be capable of rapidly closing itself in cases where a minimal overpressure enters the downstream passageway.

Another requirement of the check valves used in the medical applications in question consists in simple and low-cost realisation.

As an example, a solution that partially responds to these requirements is described and illustrated in U.S. Pat. No. 5,617,897. Here, the diaphragm has an annular peripheral section held axially between the first and second tubular elements, a central section acting like a valve obturator, and openings between the peripheral section and the central section. In this solution, it can be noted that the valve's annular seat has an annular projection with a tapered border against which the central section of the diaphragm rests when the check valve is the closed position. A predetermined overpressure in the upstream passageway causes the diaphragm to flex due to its elastic stretching and the resulting passage of fluid from the upstream passageway to the downstream passageway via the diaphragm opening.

This solution has various drawbacks. First of all, the realisation of the projection with a tapered border in the first tubular element, for supporting the central section of the diaphragm, entails certain constructional complications. In addition, the difference in elasticity between the tapered border and the central section of the diaphragm can produce permanent local deformations on the diaphragm that reduce the reliability of check valve's hermetic closure, with the risk of undesired reflux of fluid from the downstream passageway to the upstream passageway. Also, because the separation of the central section of the diaphragm from the valve seat of the first tubular element when the check valve is opened, is effected by elastically stretching the diaphragm, the peripheral section of which is blocked between the first and second tubular elements, the calibration of the check valve is dependent upon the elasticity characteristics of the diaphragm. As a consequence, should the elasticity of the diaphragm undergo variations during manufacture (material characteristics, moulding parameters, etc.), calibration can be subject to significant and therefore critical variations.

Other known solutions are described and illustrated in European patent application EP-A-0247824, patent U.S. Pat. No. 5.727.594 and European patent application EP-A-0934757. In all of these instances, the diaphragm has an annular peripheral section placed axially between the first and second tubular elements, a disc-shaped central section acting like a valve obturator with the said valve seat, and openings between the peripheral section and the central disc.

These known solutions have a series of common elements: first of all, the annular peripheral section of the diaphragm is thicker and seated in a complementary annular seat formed between the first and second tubular elements. Moreover, this thicker annular peripheral section is axially blocked within the seat, acting like a seal.

In the second place, when the valve is in the closed position, the membrane exhibits a more or less deformed shape in the axial direction, in the sense that the central disc section and the peripheral section are not mutually coplanar.

In addition to a more or less significant amount of axial space occupied the valve, these realisations also have constructional problems deriving from difficulties in assembling the diaphragm between the first and second tubular elements.

SUMMARY OF THE INVENTION

The object of the present invention is that of resolving these inconveniencies, this objective being principally achieved via the characteristics defined in claim 1, i.e. the fact that the said disc is moulded with a thin circumferential sealing lip, projecting axially from the side of the disc facing the said valve seat.

This solution allows the inconveniencies of the previous techniques to be eliminated and avoids the need to create an axial annular projection in the first tubular element to delineate the valve seat (as in the case of the already cited document U.S. Pat. No. 5,617,897), which simplifies the overall construction of the check valve.

The disc is conveniently moulded with an identical, axially projecting, circumferential sealing lip on the opposite face to render the diaphragm completely symmetrical, which obviously simplifies assembly operations for the check valve.

According to another aspect of the invention, the disc is connected to the peripheral section via a crown with arched arms, the aforesaid openings being between the arched arms. In this way, movement of the central disc, which forms the valve obturator, between the open and close positions relative to the valve seat is realised via the geometric lengthening of the said arched arms to a substantially straight condition and, respectively, by the said arms returning to the initial arched configuration. Due to their arched shape, the lengthening of the arms does not cause any significant elastic deformation to the diaphragm, and so the movement of the diaphragm's central disc away from the valve seat, that is the opening of the check valve, has a substantially linear characteristic. This linearity, repeatable over time, renders calibration of the check valve in conformity with the invention extremely straightforward by simply regulating the assembly preload on the diaphragm between the first and second tubular elements.

In addition, the fact that motion of the diaphragm's central disc when opening occurs due to the straightening of the said arched arms, or rather following their geometrical lengthening without substantial elastic stretching, renders the opening of the check valve in conformity with the invention softer and more gradual with respect to conventional check valves for a given preload.

According to a further characteristic of the invention, the said arched arms conveniently have a concave longitudinal edge and convex longitudinal edge with different curvature radii, with the former larger than the second. This characteristic allows each arm to be endowed with rapid return characteristics in the starting curve condition, and hence rapid return of the diaphragm's central disc to the closed valve position. It is possible to change the valve's calibration by conveniently adjusting the radius values for the concave and convex edges at the time of manufacture: reducing the difference between these radii results in softer valve closing characteristics.

The diaphragm is normally produced via liquid silicone injection moulding: in such cases, moulding can be profitably realised with a central injection point (i.e. in correspondence with the centre of the diaphragm disc), which avoids any kind of interruption or discontinuity on either of the disc's sealing lips. This ensures perfect hermetic sealing during operation when the valve is in the closed position.

According to another aspect of the invention, the said annular peripheral section can have a thickness equal to that of the said central disc. The said annular peripheral section can be inserted between the said first and second tubular elements without axial blocking and, in the valve closed position, the said diaphragm can have a planar shape.

This characteristic simplifies manufacture of the check valve, above all in relation to the production of the diaphragm and its assembly with the tubular elements, as well as improving operating reliability.

BRIEF DESCRIPTION OF THE DRAWINGS

Further characteristics and advantages will be revealed during the detailed description that follows and makes reference to the enclosed drawings, which are supplied purely as a non-limitative example, wherein:

FIG. 5 is a similar view to that of FIG. 1, showing the application of a check valve in conformity with the invention to a Y connector for medical infusion lines and the like.

FIG. 1A is a schematic, axial section view that shows a tube-to-tube axial fitting for medical infusion lines, incorporating a check valve in conformity with a second embodiment of the invention, corresponding to that defined in claims 12–22.

FIG. 2A is a larger scale plan view in relation to arrow II in FIG. 1A.

FIG. 3A is an axial section view along the III—III line of FIG. 2A.

DETAILED DESCRIPTION OF THE INVENTION

Figure 1:
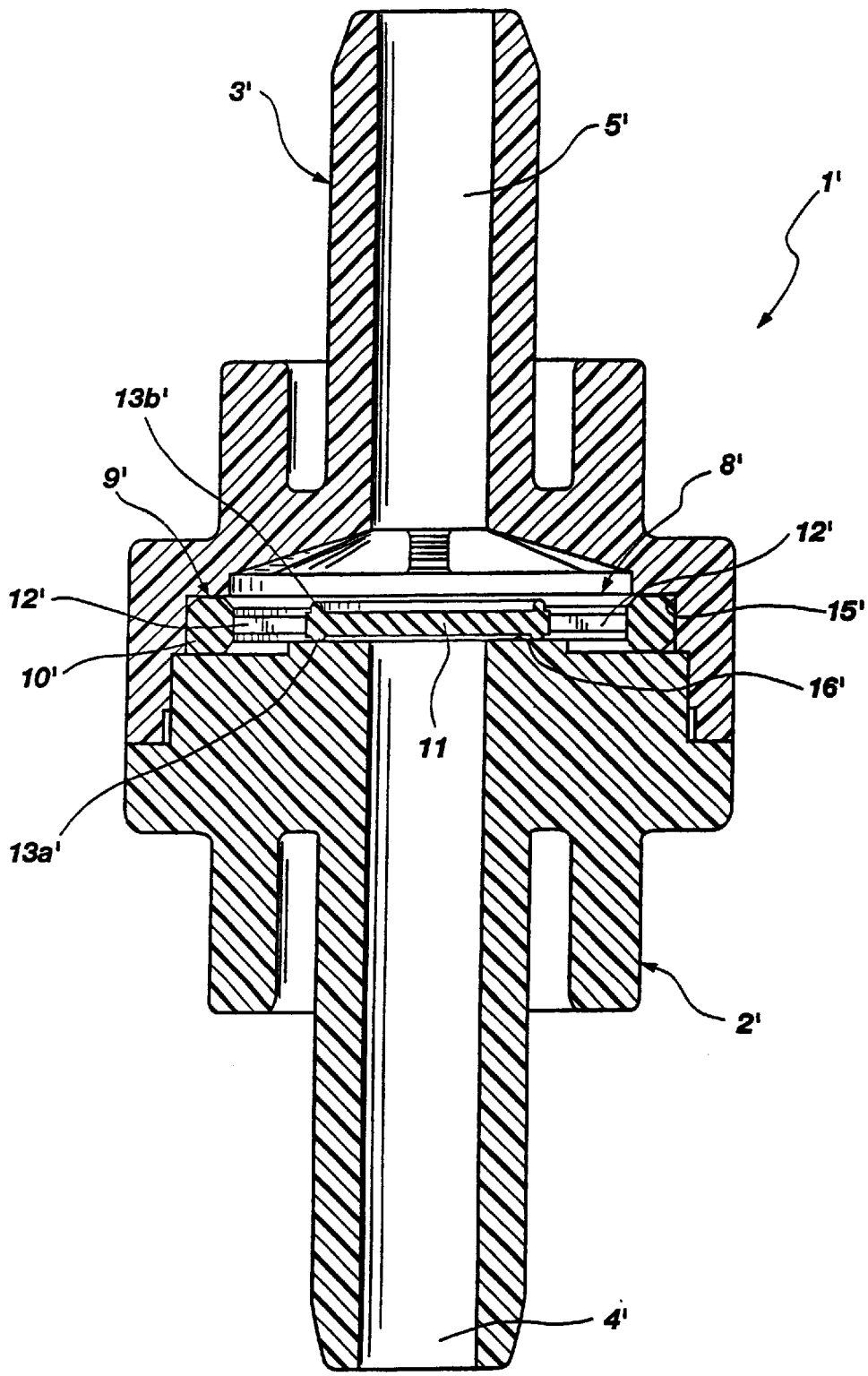
FIG. 1 is a schematic, axial section view that shows a Luer-type axial fitting for medical infusion lines, incorporating a check valve in conformity with the first form of implementation preferred by the invention, corresponding to that defined in claims 1–11.
Figure 4:
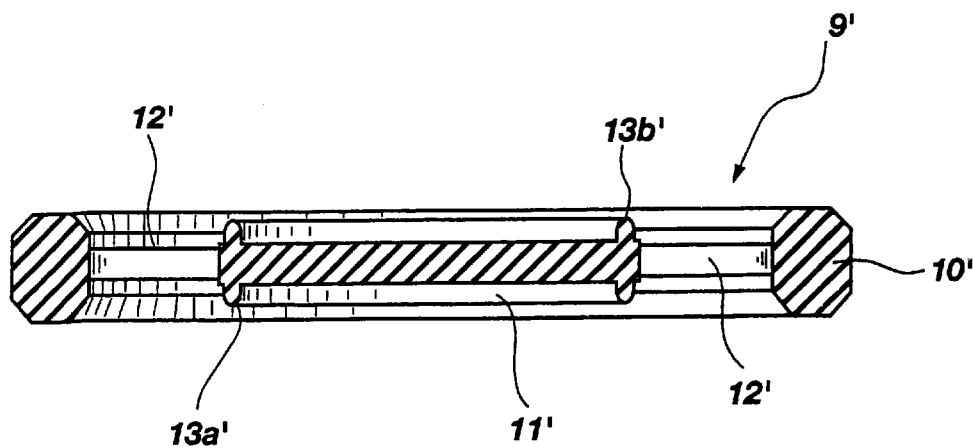
FIG. 4 is a diametrical section view along the IV—IV line of FIG. 3.
Figure 4A:
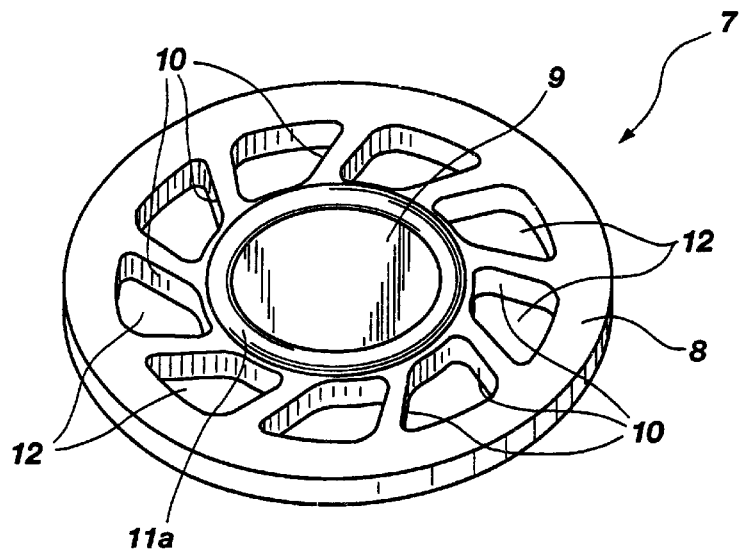
FIG. 4A is a perspective of the valve diaphragm in FIGS. 1A–3A.
Figure 5A:
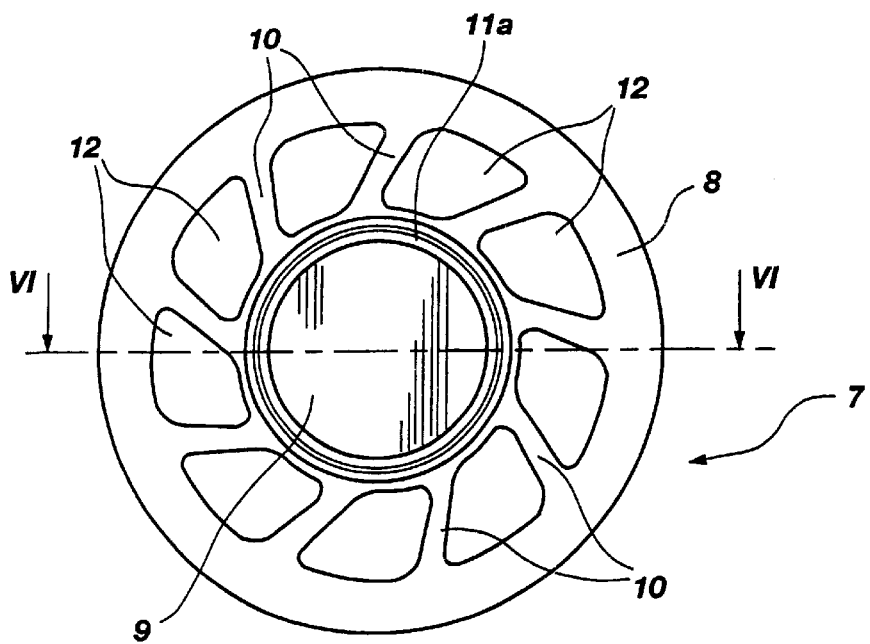
FIG. 5A is a plan view of FIG. 4A.
Figure 6:
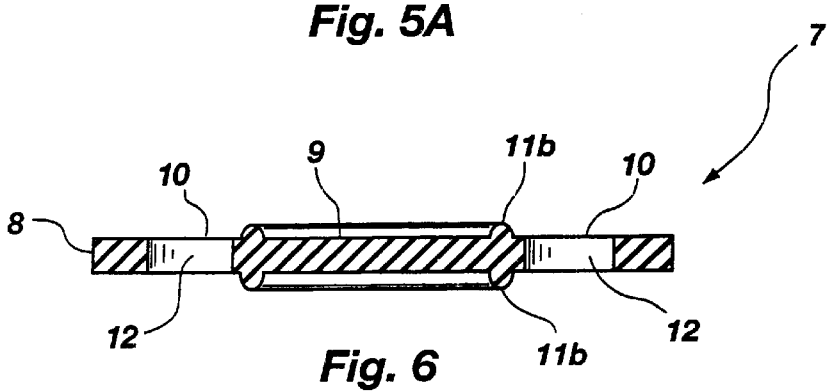
FIG. 6 is a cross-section view along the VI—VI line of FIG. 5A.

With initial reference to FIGS. 1 and 4, item (1') indicates the Luer-type axial fitting for medical infusion and transfusion lines and the like, as a whole. The fitting (1') includes, in the generally known manner, a first tubular connector (2') and a second tubular connector (3'), both normally made of a suitable moulded thermoplastic material, such as polycarbonate, and coaxially joined together in a permanent manner, via ultrasonic bonding or gluing for example.

The first and second tubular connectors (2', 3') respectively define an upstream passageway or inlet passageway (4') and a downstream passageway or outlet passageway (5'), which can be connected to the respective tubing sections of a medical infusion line.

A check valve, which constitutes the specific subject of the present invention and is generically indicated as item (8'), is mounted between the upstream passageway (4') and the downstream passageway (5').

The check valve (8') basically consists of a transversal diaphragm (9') realised via liquid silicone injection moulding.

Figure 2:
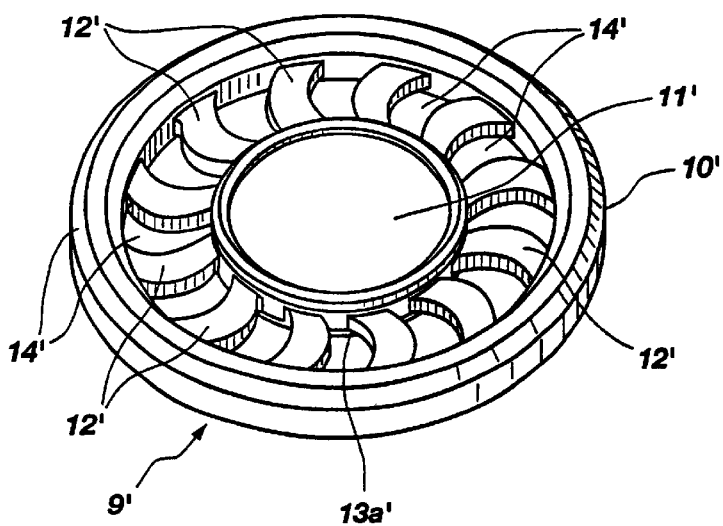
FIG. 2 is a larger scale perspective that shows the diaphragm of the check valve represented in FIG. 1.

The diaphragm (9'), shown in greater detail in FIGS. 2 and 4, has a circular shape on the whole and incorporates an annular peripheral section (10'), a circular disc-shaped central section (11') and an intermediate crown of arms (12') that integrally connect the central disc (11') with the peripheral ring (10').

The peripheral ring (10') has an axial thickness greater than that of the central disc (11'), as shown in FIG. 4, thus defining a thickened ring with an opportune, but not obligatory, rectangular cross-section with bevelled edges.

The central disc (11') has a thin, axially projecting, circumferential sealing lip (13a', 13b') on the edge of each of it faces.

The arms (12') are arranged radially and spaced out between each other to form a crown of openings (14'). According to a specific characteristic of the invention, each arm (12') has an arched shape with one concave longitudinal edge (12a') and one convex longitudinal edge (12b'). The curvature radii of the longitudinal edges (12a', 12b') of each arm (12') can be substantially the same, or conveniently diverse: in particular, the curvature radius of the convex edge (12b') should preferably be smaller than the curvature radius of the concave edge (12a').

Returning to FIG. 1, the thickened peripheral ring (10') of the diaphragm (9') is located in an internal seat (15') defined by the tubular connectors (2', 3') and the central disc (11') is arranged in correspondence with the internal extremity of the upstream passageway (4'). This central disc (11') with the relative sealing ring (13a' or 13b', indifferently) acts as a valve obturator with an annular valve seat (16') encircling the internal extremity of the upstream passageway (4'). The annular valve seat (16) is simply defined by a flat axial step on the tubular connector 2', without any annular protrusions or projections.

Operation of the check valve (8') is as follows.

As has already been clarified, the check valve (8') is normally closed: in this condition, shown in FIG. 1, the diaphragm (9') assumes a substantially planar configuration with respect to the central disc (11'), resting against the annular valve seat (16') via the relative sealing lip (13a' or 13b'). The hermetic sealing of the internal extremity of the upstream passageway (4') is guaranteed by the frontal contact between the lip (13a' or 13b') and the valve seat (16') under pressure due to the elastic preloading of the diaphragm (9') during assembly between the connectors (2', 3') of the fitting (1'). This preload can be calibrated, at the time of manufacture, by conveniently varying the axial distance of the valve seat (16') with respect to the internal extremity of the upstream passageway (4').

Figure 3:
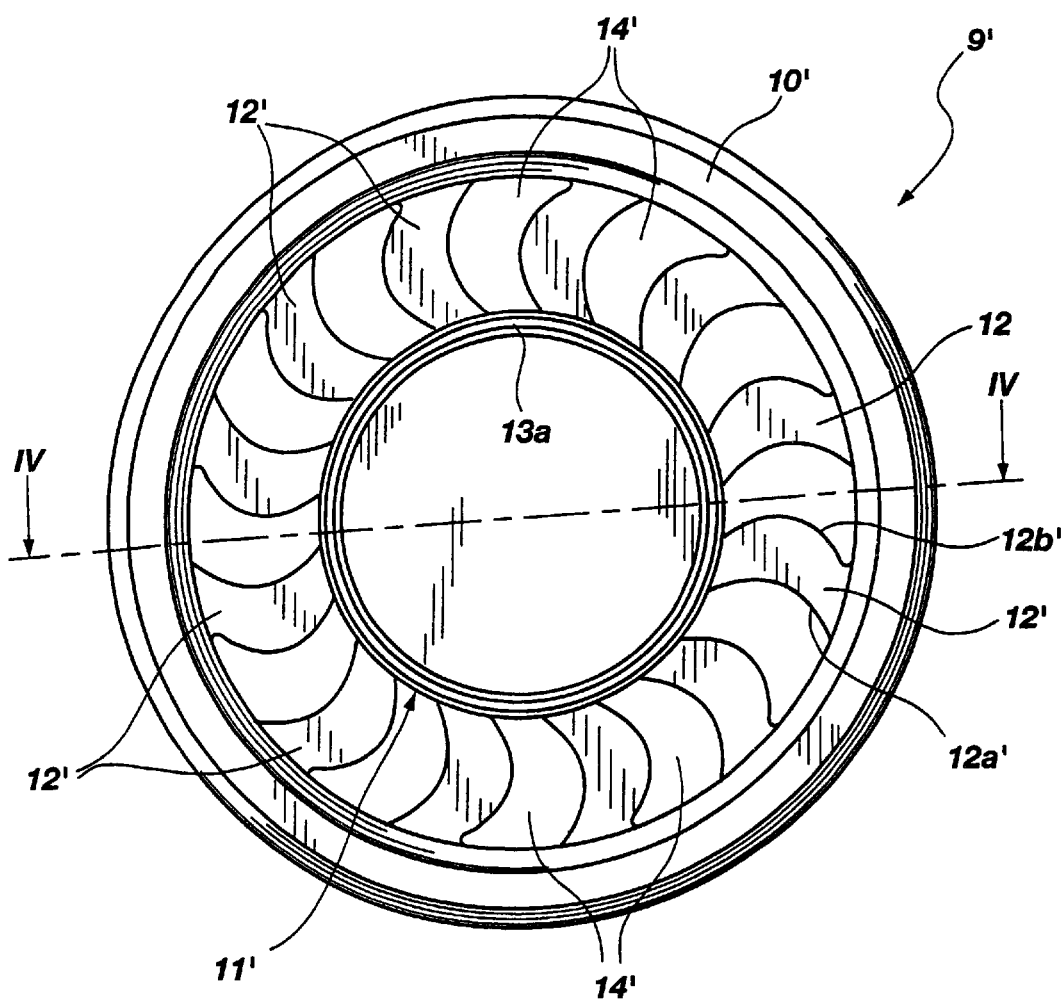
FIG. 3 is a larger scale plan view of FIG. 2.

In this closed state, the check valve (8') effectively prevents any reflux from the downstream passageway (5') to the upstream passageway (4'), since any increase in pressure inside the downstream passageway (5') produces an additional axial force on the sealing lip (13a' or 13b') against the annular valve seat (16'). When an overpressure exceeding a predetermined threshold, evidently correlated with the assembly preloading of the diaphragm (9'), develops inside the upstream passageway (4'), the check valve (8') passes immediately from the closed position to the open position as a result of the disc (11') and relative lip (13a' or 13b') moving axially away from the valve seat (16'). This movement is rendered possible via the straightening effect of the arms (12'), from the initial arched state of FIGS. 2–4 to a more or less elongated position. In all cases, this lengthening is almost exclusively geometric, with very limited elastic stretching of the arms (12') taking place.

The shape of the thin lip (13a' or 13b') permits immediate separation of the disc (11') from the valve seat (16'), without the risk of unwanted adherence. This effect is further emphasised due to the fact that the lengthening of the arched arms (12') gives rise to twisting moment that, although slight, imparts a small rotation to the disc (11') when it moves axially away from the valve seat (16'). In practice therefore, the opening motion of the disc (11') is slightly helical.

The upstream passageway (4') thus communicates with the downstream passageway (5') via the openings (14') between the arms (12') of the diaphragm (9').

The check valve (8') immediately returns to the closed position when the pressure balance between the upstream passageway (4') and downstream passageway (5') is re-established, or in the case of overpressure in the downstream passageway (5'), by to the disc (11') returning to the rest state with the relative lip (13a'or 13b') against the valve seat (16'). In this phase, the arms (12') return to their initial arched configuration, contributing to the rapid and prompt return of the disc (11') to the closed position. The greater the curvature radius of the convex edges (12b') with respect to the concave edges (12a'), the greater this effect will be.

It should be noted that in the above-described arrangement, the thickened ring (10') of the diaphragm (9') does not require tight axial blockage in the seat (15'). In fact, a certain amount of axial clearance can exist between the faces of the ring (10') and one and/or the other axial surfaces of the connectors (2', 3') that delimit the seat (15'). This, together with the substantial absence of elastic stretching on the arms (12'), permits particularly smooth opening of the obturator (11), but without influencing immediacy or promptness.

The check valve in conformity with the invention is conveniently calibrated for opening at pressure levels ranging from 0.005 up to 0.2 bar. It can also be used to advantage for applications such as anti-syphon valves, where it can be calibrated for pressures of around 1–2 psi.

Figure 5:
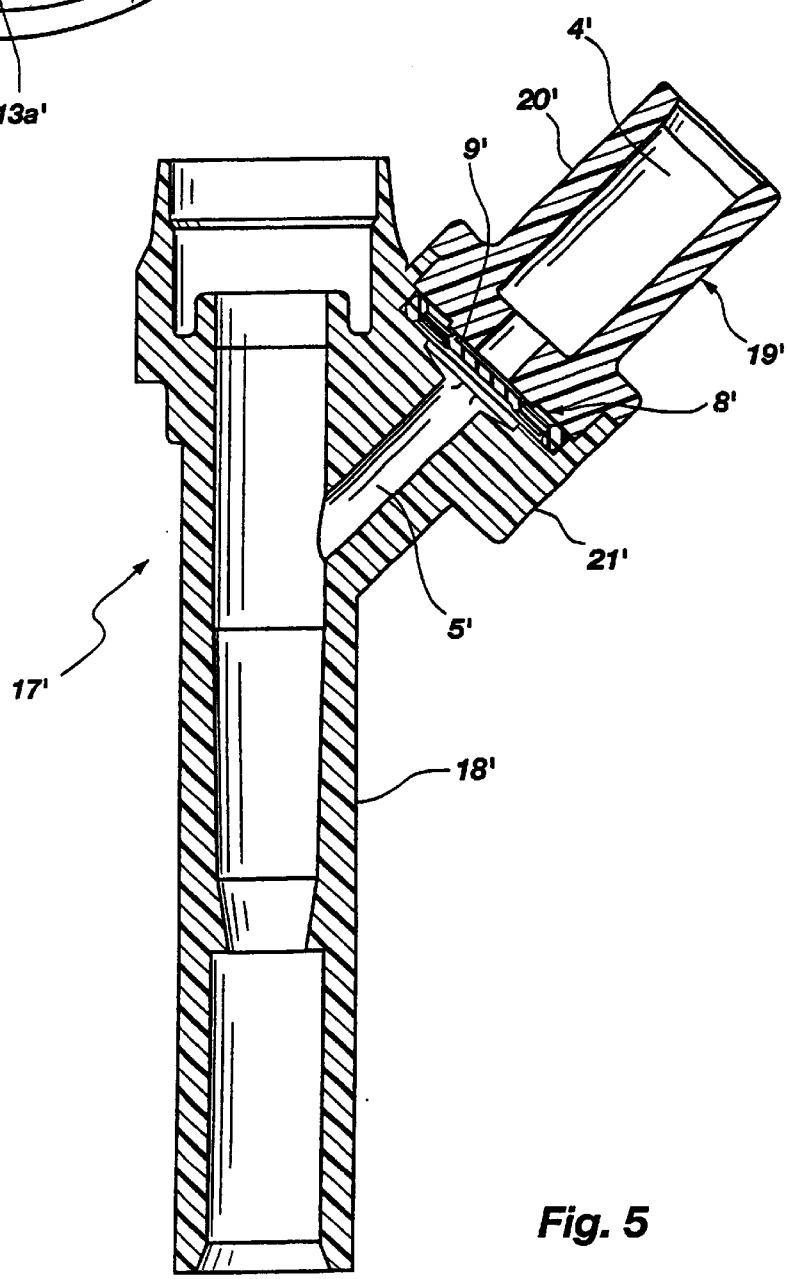

FIG. 5 illustrates the application of the check valve (8") in conformity with the invention to a Y piece (17') for medical infusion lines and the like, basically consisting of, in the generally known manner, a main tubular connector (18') and a side connector (19') that forms an acute angle with the main connector (18'). This side connector (19') is formed by a first tubular element (20') coaxially joined in a permanent manner inside a second tubular element (21'), which in turn forms an integral part of the main connector (18'). The first and second tubular connectors (20', 21') respectively define an upstream passageway or inlet passageway (4') and a downstream passageway or outlet passageway (5') for the immission of a fluid from the side connector (19') into the main connector (18'), e.g. via the insertion of a needle-less injection device in the tubular element (20'). The check valve (8'), the structure of which is completely identical to that previously described with reference to FIGS. 1 to 4, is inserted between the tubular elements 20' and 21', and its relative operation is completely identical to that already described.

A second embodiment of the invention will now be disclosed with reference to FIGS. 1A–5A and 6–15.

Referring initially to FIGS. 1A–3A, item 1 indicates a tube-to-tube axial fitting for medical infusion and transfusion lines and the like, as a whole. It should be immediately noted that the fitting could be set up, in the conventional manner, for Luer-tube, tube-Luer and Luer-Luer type connections.

The fitting (1) includes, in the generally known manner, a first tubular connector (2) and a second tubular connector (3), both normally made of a suitable moulded thermoplastic material, such as polycarbonate or the like, and coaxially joined together in a permanent manner, via ultrasonic bonding or gluing for example.

The first and second tubular connectors (2, 3) respectively define an upstream passageway or inlet passageway (4) and a downstream passageway or outlet passageway (5), which can be connected to the respective tubing sections of a medical infusion line.

A check valve, which constitutes the specific subject of the present invention and is generically indicated as item 6, is mounted between the upstream passageway (4) and the downstream passageway (5).

The check valve (6) basically consists of a transversal diaphragm (7), conveniently realised via liquid silicone injection moulding and illustrated in greater detail in the first form of implementation shown in FIGS. 4A–6.

The diaphragm (7) has a circular shape on the whole and incorporates an annular peripheral section (8), a circular disc-shaped central section (9) and an intermediate crown of evenly spaced arms (10) that integrally connect the central disc (9) with the peripheral ring (8).

According to an initial characteristic of the invention, the thickness of the peripheral ring (8) is identical to that of the arms (10), which in turn is the same as that of the central disc (9), except for the fact that the latter is moulded with a thin, axially projecting, circumferential sealing lip (11a, 11b) on the edge of each of it faces.

In the forms of implementation shown if FIGS. 4A–6, the arms (10) are not radially oriented, but arranged obliquely and asymmetrically with respect to the diametrical planes of the diaphragm (7). As a result, the spaces between the oblique arms (10) define a crown of openings (12) that have a quadrangular shape in plan, trapezoidal in this case, with rounded vertices.

Returning now to FIG. 3A, the peripheral ring (8) is located in an annular radial seat (13) on the second tubular connector (3) and facing the front wall (14) of the first tubular connector (2). The seat (13) is axially spaced away from the wall (14) by a distance greater than the thickness of the peripheral ring (8).

The central disc (9) of the diaphragm (7) faces the internal extremity of the upstream passageway (4), with the relative sealing lip (11a or 11b, indifferently) resting against the zone of the front wall (14) that encircles the internal extremity of the upstream passageway (4) and defines the annular valve seat (15), and acts as a valve obturator.

With this arrangement, the peripheral ring section (8) of the diaphragm (7) can be freely inserted between the first and second tubular elements (2, 3) without axial blocking. In the normally closed position of the valve (6), in which the said sealing lip (11a or 11b) is held against the annular valve seat (15), the arms (10) are not deformed to any significant extent (except for very small elastic preloads during assembly of the obturator (7)). In consequence, in the normally closed position of the valve (6), the diaphragm (7) exhibits a planar configuration as shown in FIG. 3A.

Operation of the check valve (6) is as follows.

As has already been clarified, the check valve (6) is normally closed: the pressure with which the relative sealing lip (11a or 11b, indifferently) of the diaphragm (7) is held against the annular seat (15) to seal the valve can be calibrated, at the time of manufacture, by conveniently varying the axial distance between the annular valve seat (15) on the front wall (14) of connector 2 and the annular seat (13) on connector 3.

In this closed state, the check valve (7) effectively prevents any reflux from the downstream passageway (5) to the upstream passageway (4), since any increase in pressure inside the downstream passageway (5) produces an additional axial force on the sealing lip (11a or 11b) against the annular valve seat (15). When an overpressure exceeding a predetermined threshold, evidently correlated with the assembly preloading of the diaphragm (7), develops inside the upstream passageway (4), the check valve (6) passes immediately from the closed position to the open position as a result of the disc (9) and relative lip (11a or 11b) moving axially away from the valve seat (15). This movement is rendered possible via the flexion or elastic stretching of the arms (10) and permits immediate separation of the sealing lip (11a or 11b) of the disc (9) from the valve seat (15), without the risk of unwanted adherence. This effect is further emphasised due to the previously described oblique arrangement of the arms (10), which to gives rise to twisting moment that, although slight, imparts a small rotation to the disc (9) when it moves axially away from the valve seat (15). In practice therefore, the opening motion of the disc (9) can be considered slightly helical.

The upstream passageway (4) thus communicates with the downstream passageway (5) via the openings (12) between the arms (10)

The check valve (6) immediately returns to the closed position when the pressure balance between the upstream passageway (4) and downstream passageway (5) is re-established, or in the case of overpressure in the downstream passageway (5), by the disc (9) returning to the rest state with the relative lip (11a or 11b) against the valve seat (15). In this phase, the arms (10) return to their initial non-deformed configuration, contributing to the rapid and prompt return of the disc (9) to the closed position.

The homogenous thickness of the diaphragm (7), together with the characteristic whereby its peripheral section (8) is not axially blocked, contributes to render the opening and closing motion of the disc (9) particularly smooth, but without influencing immediacy or promptness.

In addition, the diaphragm (7) exhibits a completely symmetrical configuration and is therefore reversible, in the sense that during assembly of the valve (6) it can be positioned with either lip 11a or lip 11b facing the valve seat (15).

The check valve in conformity with the invention is opportunely calibrated for opening at pressure levels ranging from 0.005 up to 0.2 bar and above. It can also be used to advantage for applications such as anti-syphon valves, in which case it can be calibrated for pressures of around 1–5 psi. In addition to axial fittings, the check valve (6) in conformity with the invention can also be applied with advantage in the case of Y pieces.

FIGS. 7–9, 10–12 and 13–15, in which identical or similar parts to those previously described in reference to FIGS. 1A–5A and 6 are indicated using the same numeric references, illustrate three variants of the diaphragm (7) and check valve (6) in conformity with the invention.

Figure 7:
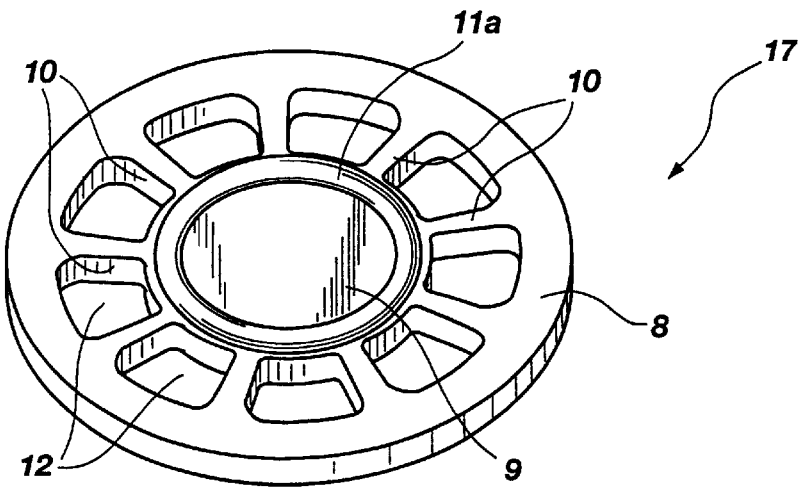
FIG. 7 illustrates a first variant of FIG. 4A.
Figure 8:
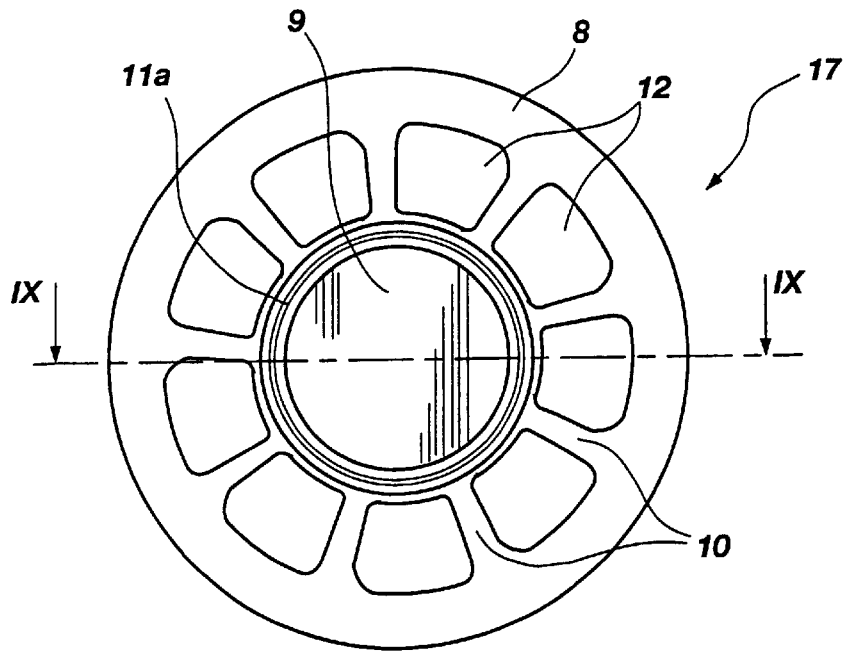
FIG. 8 is a plan view of FIG. 7.
Figure 9:
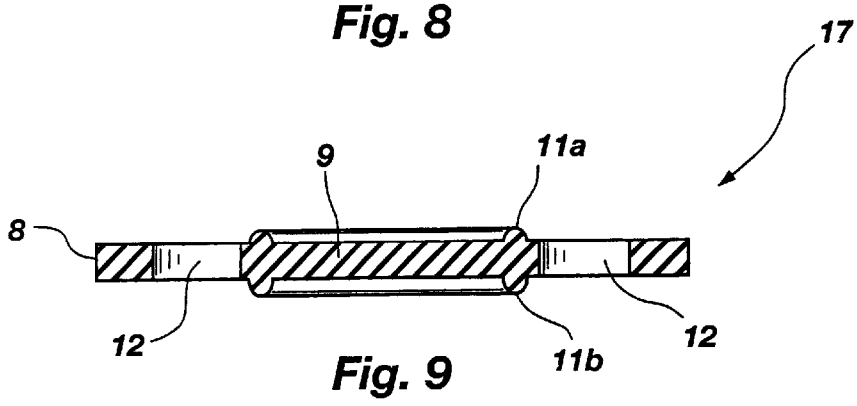
FIG. 9 is a cross-section view along the IX—IX line of FIG. 8.

In the case of FIGS. 7–9, the diaphragm, indicated in its entirety as item 17, has radially oriented arms (10) resulting in openings (12) that, in plan view, have an isosceles trapezium form with, in this case as well, rounded vertices. In this case, the arms (10) are also arranged in an asymmetric manner.

Figure 10:
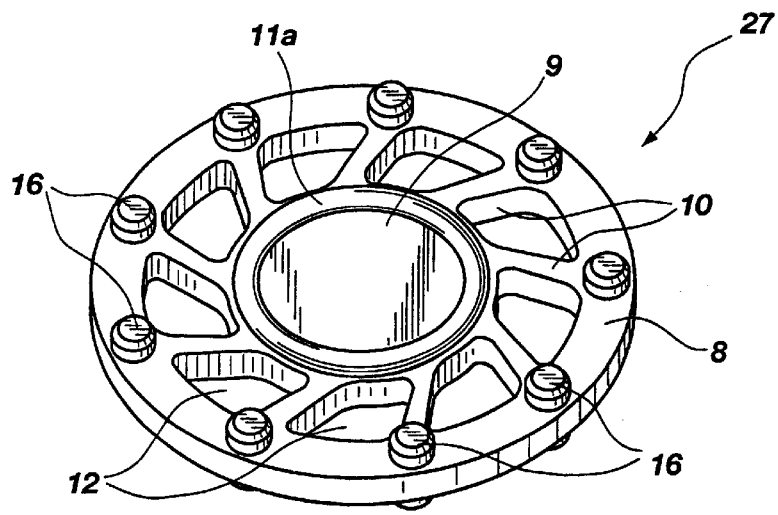
FIG. 10 illustrates a second variant of FIG. 4A.
Figure 12:
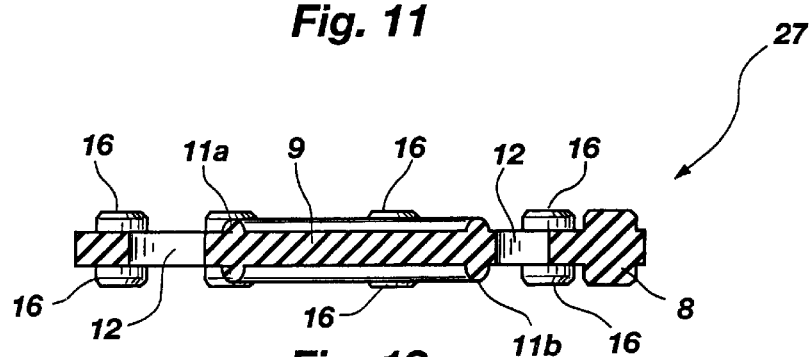
FIG. 12 is a cross-section view along the XII—XII line of FIG. 11.

In the case of FIGS. 10 and 12, the diaphragm, indicated as item 27, only differs from the that in FIGS. 4A–6 in that its annular peripheral section (8) is moulded on one face, or more conveniently on the other face as well, with a crown of cylindrical axial projections (16), substantially cylindrical in shape, positioned in correspondence to the external radial extremity of the oblique arms (10).

Figure 11:
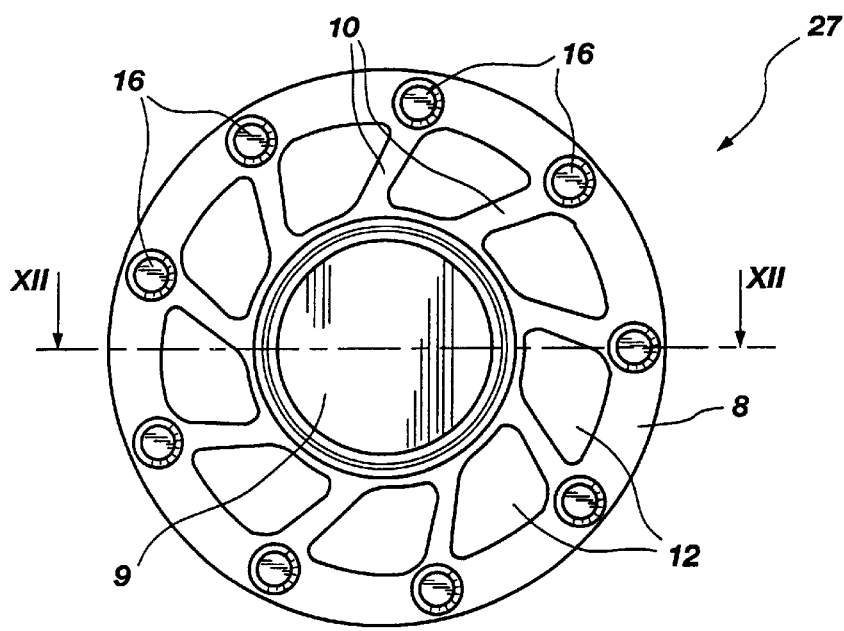
FIG. 11 is a plan view of FIG. 10.
Figure 13:
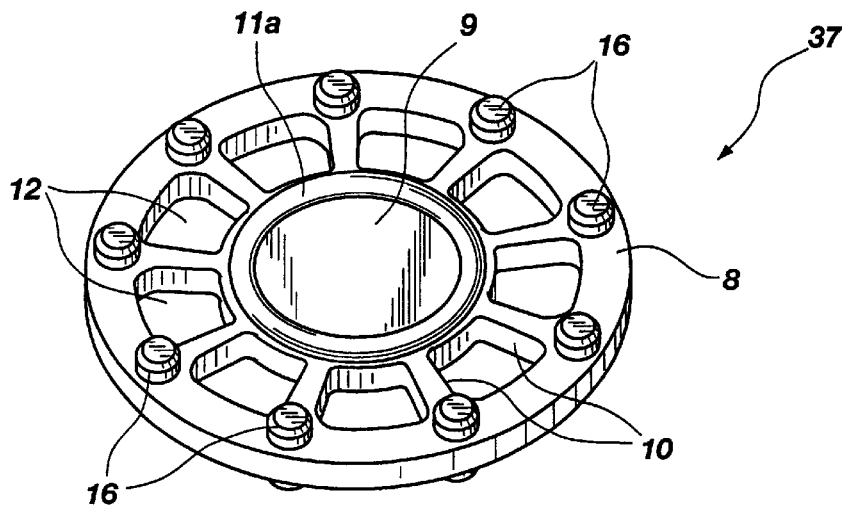
FIG. 13 illustrates a third variant of FIG. 4A.
Figure 14:
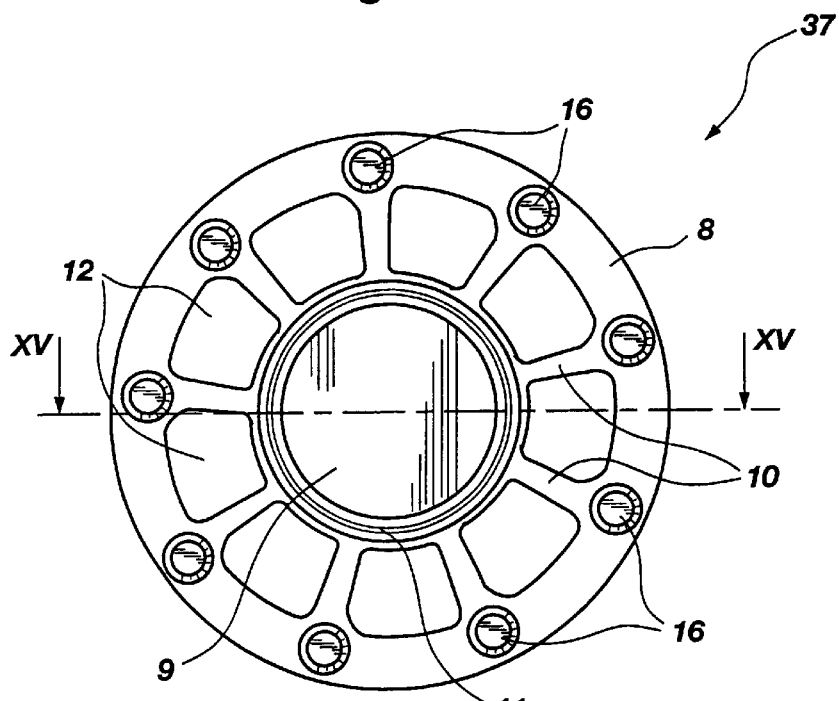
FIG. 14 is a plan view of FIG. 13.
Figure 15:
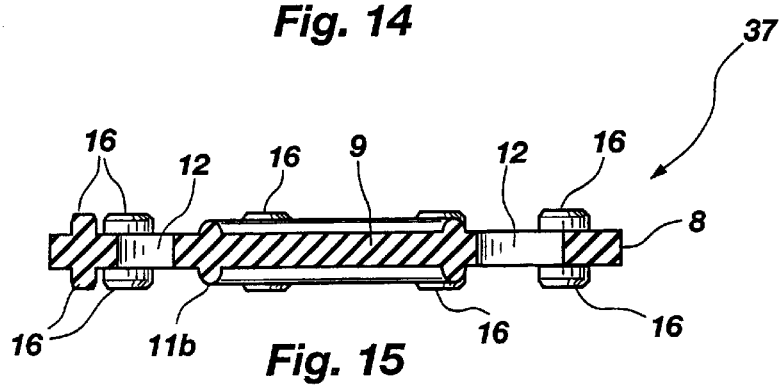
FIG. 15 is a cross-section view along the XV—XV line of FIG. 14.

Finally, in the case FIGS. 13 to 15, the diaphragm, indicated as item 37, is identical to that illustrated in FIGS. 7 to 9 except for the fact that, as in the case of diaphragm 27 in FIGS. 10 to 12, the peripheral section (8) is moulded on both faces with axial projections (16) positioned in correspondence to the external radial extremity of the radial arms (10).

Naturally, it being understood that the principle of the invention, the constructional details and the forms of realization could be extensively changed with respect to that described and illustrated without leaving the scope of this invention, as defined in the following claims.

What is claimed is:

1. A check valve for medical infusion lines comprising:
   a first and a second tubular element that respectively define an upstream passageway and a downstream passageway, said first and second tubular elements being mutually coaxial to each other, and
   a diaphragm of elastically deformable material transversely positioned between said first and second tubular elements, said diaphragm acting as a fluid seal in combination with an annular valve seat of said first tubular element to keep the said check valve normally closed,
   wherein a predetermined fluid pressure in said upstream passageway causes flexion of said diaphragm and the resulting opening of said check valve, and wherein said diaphragm has an annular peripheral section, a disc-shaped central section which acts as a valve obturator and openings between said annular peripheral section and said disc-shaped central section, said disc-shaped central section having a first side facing said valve seat and a first thin circumferentially continuous sealing lip projecting axially from said first side of said central section and a second thin circumferentially continuous sealing lip projecting axially from a second side of said central section.

2. A valve according to claim 1, wherein said thin circumferentially continuous sealing lips are identical to one another and wherein said diaphragm has a symmetrical arrangement.

3. A valve according to claim 1, comprising a crown of arched arms connecting said disc-shaped central section to said peripheral annular section.

4. A valve according to claim 3, wherein said openings are delimited between said arched arms.

5. A valve according to claim 4, wherein said arched arms have a concave longitudinal edge and a convex longitudinal edge with different curvature radii.

6. A valve according to claim 5, wherein said convex edge has a radius of curvature greater than that of the said concave edge.

7. A valve according to claim 1, wherein said annular peripheral section is axially retained between said first and second tubular elements.

8. A valve according to claim 7, wherein said annular peripheral section is composed of a ring having a greater thickness than that of said central disc.

9. A valve according to claim 8, wherein said ring is fitted between said first and second tubular elements without axial blocking.

10. A valve according to claim 9, wherein said ring has a quadrangular cross-section with rounded corners.

11. A valve according to claim 1, wherein said diaphragm is formed by a body of injection moulded liquid silicone with a central injection point.

12. A valve according to claim 1, wherein said annular peripheral section has the same thickness as said disc-shaped central section, said annular peripheral section being fitted between said first and second tubular elements without axial blocking, and said diaphragm having a planar configuration when the valve is in the closed position.

13. A valve according to claim 12, comprising a crown of arched arms connecting said disc-shaped central section to said annular peripheral section.

14. A valve according to claim 13, wherein said arched arms are arranged in an asymmetric manner.

15. A valve according to claim 14, wherein said arched arms are radially oriented with respect to said disc-shaped central section.

16. A valve according to claim 14, wherein said arms are obliquely oriented with respect to a diametric plane of the diaphragm.

17. A valve according to claim 13, wherein said openings are delimited between said arched arms.

18. A valve according to claim 17, wherein said openings have a trapezoidal shape in plan.

19. A valve according to claim 13, wherein said arms have a same thickness as that of said annular peripheral section of the diaphragm.

20. A valve according to claim 13, wherein said annular peripheral section has a crown of axial projections on at least one of its faces.

21. A valve according to claim 20, wherein said axial projections are provided on both faces of said annular peripheral section.

22. A valve according to claim 21, wherein said projections are arranged in angular correspondence with external radial ends of said arched arms.

23. A check valve for medical infusion lines comprising:

a first and a second tubular element that respectively define an upstream passageway and a downstream passageway, said first and second tubular elements being mutually coaxial to each other, and a diaphragm of elastically deformable material transversely positioned between said first and second tubular elements, said diaphragm acting as a fluid seal in combination with an annular valve seat of said first tubular element to keep said check valve normally closed, wherein a predetermined fluid pressure in said upstream passageway causes flexion of said diaphragm and the resulting opening of said check valve, wherein said diaphragm has an annular peripheral section, a disc-shaped central section which acts as a valve obturator and openings between said annular peripheral section and said disc-shaped central section, and a crown of arched arms connecting said disc-shaped central section to said annular peripheral section, said disc-shaped central section having a side facing said valve seat and a thin circumferential sealing lip projecting axially from said side of said disc shaped central section, said annular peripheral section having the same thickness as said disc-shaped central section, said annular peripheral section being fitted between said first and second tubular elements without axial blocking, said annular peripheral section having a crown of axial projections on at least one of its faces and said diaphragm having a planar configuration when the valve is in a closed position.

24. A valve according to claim 23, wherein said axial projections are provided on both faces of said annular peripheral section.

25. A valve according to claim 24, wherein said projections are arranged in angular correspondence with external radial ends of said arched arms.

* * * * *